United States Patent [19]

Hasegawa et al.

[11] Patent Number: 4,914,035
[45] Date of Patent: Apr. 3, 1990

[54] PROCESS FOR PRODUCING SIALIC ACID DERIVATIVES

[75] Inventors: Akira Hasegawa; Makoto Kiso, both of Gifu, Japan

[73] Assignee: Wako Pure Chemical Industries, Ltd., Osaka, Japan

[21] Appl. No.: 352,594

[22] Filed: May 16, 1989

[30] Foreign Application Priority Data

Aug. 12, 1988 [JP] Japan .................................. 63-201107

[51] Int. Cl.[4] ........................ C07G 3/00; C07G 37/00; C07H 23/00; C07H 1/00
[52] U.S. Cl. ..................................... 536/18.6; 536/54; 536/122; 536/124; 536/121
[58] Field of Search ................ 536/18.6, 54, 122, 124, 536/121, 53, 55.2, 55.3

[56] References Cited

FOREIGN PATENT DOCUMENTS 63-41494 2/1988 Japan .

OTHER PUBLICATIONS

Carbohydrate Research 163 (1987), 209–225; Numata, Masaaki Sugimoto, Mamory; Kioke, Katsuya; and Ogawa, Tomoya *Total Synthesis of Sialosylcerebroside, GM4*.
Tetrahedron Lett., 27, 5229–5232 (1986); Okamoto, Kaoru; Kondo, Tadao; Goto, Toshio; *Synthesis of (α2-9)and (α2-8) Linked Neuraminylneuraminic Acid Derivatives*[1].
Tetrahedron Lett., 27, 5233–5236 (1986); Okamoto, Kaoru; Kondo, Tadao; Goto, Toshio; *An Effective Synthesis of α-Glycosides of N-Acetylneuraminic Acid by Use of 2β-Halo-3β-Hydroxy-4,7,8,9-Tetra-O-Acetyl-N-Acetylneuraminic Acid Methyl Ester*[1].
Tetrahedron Lett., 28, 6221–6224 (1987); Ito, Yukishige; Ogawa, Tomoya; *An Effective Approach to Stereoselective Glycosylation of N-Acetylneuraminic Acid; Use of Phenylselenyl Group as a Stereocontrolling Auxiliary*.
Chem. Ber., 99, 611–617 (1966); Kuhn, Richard; Lutz, Peter and MacDonald, Donald L.; *Synthese Anomerer Sialinsaure-Methylketoside*.
Carbohydrate Research 146 (1986) 147–153; Paulsen, Hans and von Deessen, Ulrich; *Glycosidsynthese von N-AcetylNeuraminsaure mit Sekundaren Hydroxylgruppen*.

Primary Examiner—Ronald W. Griffin
Assistant Examiner—Everett White
Attorney, Agent, or Firm—Armstrong, Nikaido, Marmelstein, Kubovcik & Murray

[57] ABSTRACT

The present invention provides a process for selective production of a 2-α-O-glycoside compound of sialic acid which is useful as a starting material or intermediate for medicines and biochemical reagents. The process comprises reacting an alkylthiosialic acid derivative represented by the formula [I]:

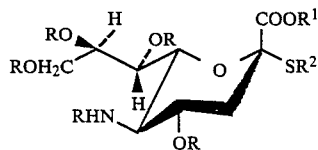

wherein R represents an acyl group and $R^1$ and $R^2$ each represents a lower alkyl group with a compound having alcoholic hydroxyl group at a low temperature in a polar solvent having no hydroxyl group in the presence of a Lewis acid selected from the group consisting of methyl triflate, trimethylsilyl triflate and dimethyl(methylthio)sulfonium triflate. The present invention further provides novel compounds.

12 Claims, No Drawings

PROCESS FOR PRODUCING SIALIC ACID DERIVATIVES

BACKGROUND OF THE INVENTION

The present invention relates to a process for selective production of a 2-α-O-glycoside compound of sialic acid useful as a starting material or an intermediate for various medicines and biochemical reagents such as gangliosides or analogues thereof.

Sialic acid is present in various tissues of living organisms and is normally present in the portion which constitutes a sugar chain as its constitutional unit through glycosidic linkage. Sialic acid is an important constitutional component of glycolipid or glycoprotein. Therefore, for the purpose of studying its function and from the viewpoint of application in medical field because of the recent attention to various physiological activities of gangliosides, investigation has been intensively made on synthesis of analogues, derivatives, glycosides of sialic acid and sialooligosaccharides have been synthesized. However, the study is only beginning and there are many problems in synthesis to be solved.

One of the problem is in conversion of sialic acid to an α-O-glycoside. That is, as is well known, in all of the naturally occurring sialic acid derivatives except for cytidine monophosphate-N-acetylneuramic acid, sialic acid bonds to sugar chain, etc. through α-O-glycoside linkage, but there have been no examples of selectively producing α-O-glycosides of sialica acid. That is Chem. Ber., 99, 611–617 (1966) discloses reacting a 2-α-Cl derivative of sialic acid as a sugar donor for formation of glycoside with a sugar derivative as an acceptor. However, the resulting glycoside is a mixture of α-glycoside and β-glycoside. Furthermore, Carbohydr. Res., 146, 147–153 (1986) and Carbohydr. Res., 163, 209–225 (1987) disclose examples of reacting the above sugar donor with a secondary hydroxyl group of sugar derivative which is an acceptor, using $Hg(CN)_2/HgBr_2$ and $Ag_2CO_3/AgClO_4$ as a catalyst, respectively. The products are also mixtures of α-glycoside and β-glycoside in which proportion of α-glycoside is smaller than that of β-glycoside in both cases. Moreover, Tetrahedron Lett., 27, 5229–5232, 5233–5236 (1986) and Tetrahedron Lett., 28, 6221–6224 (1987) disclose production of a mixture comprising a higher proportion of α-glycoside and lower proportion of β-glycoside using a sialic acid derivative having a substituent at 3-position in an attempt to preferentially produce α-glycoside. However, the product is still not satisfactory in stereoselectivity and yield and especially in the case of the reaction with secondary hydroxyl group, this cannot be practically utilized.

The inventors have already found that when an α-SMe derivative or β-SMe derivative of sialic acid as a sugar donor is reacted with a straight chain primary alcohol in dichloromethane in the presence of dimethyl(methylthio)sulfonium triflate (hereinafter referred to as "DMTST"), the corresponding β-O-glycoside of sialic acid was selectively obtained and have filed a patent application therefor. (Japanese Patent Kokai No. 63-41494).

Thus, most of O-glycosides of sialic acid which were synthetically obtained were mixtures of α-glycoside and β-glycoside and a specific case (in the case of primary hydroxyl group), only β-glycoside was selectively obtained while there have been no examples of obtaining α-glycoside selectively and in high yield. In the case of secondary hydroxyl group, there have been no examples of obtaining α-glycoside and β-glycoside selectively and in high yield.

SUMMARY OF THE INVENTION

An object of the present invention is to provide a process for producing an α-O-glycoside compound of sialic acid selectively and in higher yield which is very useful for investigating the relation between physiological activity and chemical structure of naturally occurring sialic acid derivatives such as glycoprotein and glycolipid.

Another object of the present invention is to provide a novel compound useful as starting material or intermediate for various medicines and biochemical reagents such as gangliosides, analogues thereof and the like.

DESCRIPTION OF THE INVENTION

The present invention relates to a process for producing a 2-α-O-glycoside compound of sialic acid, characterized by reacting an alkylthiosialic acid derivative represented by the formula [I]:

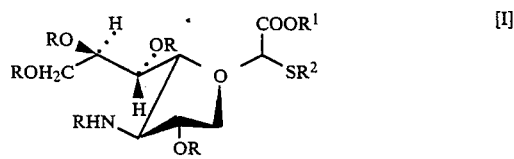

(wherein R represents an acyl group and $R^1$ and $R^2$ each represents a lower alkyl group) with a compound having an alcoholic hydroxyl group in a polar solvent having no hydroxyl group at a low temperature in the presence of a thiophilic promoter such as methyl triflate, trimethylsilyl triflate, dimethyl(methylthio)sulfonium triflate (DMTST), N-bromo succinimide, mercuric sulfate, mercuric benzoate, mercuric nitrate, phenylmercuric triflate, cupric triflate, cupric bromide, methyl sulfenyl chloride, ethyl sulfenyl chloride, methyl sulfenyl sulfenyl triflate, ethyl sulfenyl triflate, etc.

The present invention further relates to a compound represented by the following formula [II], [III], [IV], [VI], [VII] or [VIII] which is useful starting material or intermediate for various medicines and biochemical reagents such as gangliosides or analogues thereof:

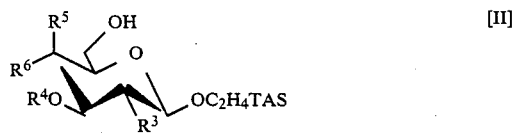

[wherein $R^3$ represents —OH, —NH$_2$, —OR$^0$ or —NHR$^0$ (R$^0$ represents an acyl group), $R^4$ represents a protecting group for hydroxyl group, one of $R^5$ and $R^6$ represents a hydroxyl group and the other represents a hydrogen atom and TAS represents trialkylsilyl group]:

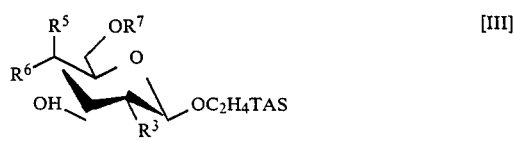

(wherein $R^7$ represents an acyl group and $R^3$, $R^5$, $R^6$ and TAS are as defined above):

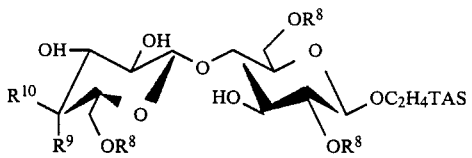 [IV]

(wherein $R^8$ represents an acyl group, one of $R^9$ and $R^{10}$ represents a hydroxyl group and the other represents a hydrogen atom and TAS is as defined above):

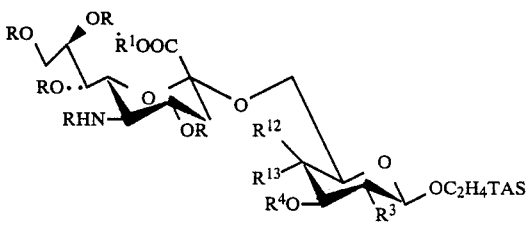 [VI]

[wherein one of $R^{12}$ and $R^{13}$ represents —$OR^{01}$ and the other represents a hydrogen atom (wherein $R^{01}$ represents an acyl group or a hydrogen atom) and R, $R^1$, $R^3$, $R^4$ and TAS are as defined above]:

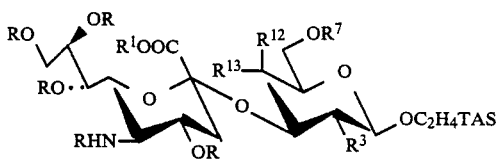 [VII]

(wherein R, $R^1$, $R^3$, $R^7$, $R^{12}$, $R^{13}$ and TAS are as defined above):

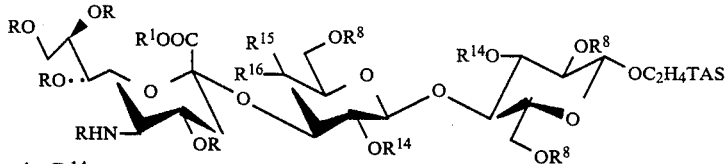 [VIII]

[wherein $R^{14}$ represents an acyl group or a hydrogen atom, one of $R^{15}$ and $R^{16}$ represents —$OR^{14}$ and the other represents a hydrogen atom (wherein $R^{14}$ is as defined above) and R, $R^1$, $R^8$ and TAS are as defined above].

R in the formulas [I], [VI], [VII] and [VIII] includes acyl groups such as acetyl group, propionyl group and butanoyl group and $R^1$ in the formulas [I], [VI], [VII] and [VIII] and $R^2$ in the formula [I] include lower alkyl groups such as methyl group, ethyl group, propyl group and butyl group, $R^3$ in the formulas [II], [III], [VI] and [VII] includes —OH, —NH$_2$, —$OR^0$ and $R^0$ includes acyl groups such as acetyl group, propionyl group, butanoyl group and benzoyl group. $R^4$ in the formula [II] includes protecting groups for hydroxyl group usually employed in this field such as acetyl group, propionyl group, butanoyl group, benzoyl group and benzyl group. One of $R^5$ and $R^6$ in the formula [II] represents a hydroxyl group and the other represents a hydrogen atom. $R^7$ in the formula [III] includes acyl groups such as acetyl group, propionyl group, butanoyl group and benzoyl group. TAS in the formulas [II], [III], [IV], [VI], [VII] and [VIII] represents trialkylsilyl groups such as trimethylsilyl group, triethylsilyl group, triisopropylsilyl group, dimethyl t-butylsilyl group. $R^8$ in the formulas [IV] and [VIII] includes acyl groups such as acetyl group, propionyl group, butanoyl group and benzoyl group. One of $R^9$ and $R^{10}$ in the formula [IV] represents a hydroxyl group and the other represents a hydrogen atom. $R^{11}$ in the formula [V] includes alkyl groups such as methyl group, ethyl group, propyl group, butyl group, pentyl group, hexyl group, heptyl group, octyl group, nonyl group, decyl group, dodecyl group, pentadecyl group, hexadecyl group and octadecyl group and these may be either straight chain or branched chain alkyl groups excluding branched chain alkyl groups which result in tertiary alcohols as the alcohol represented by the formula [V]. One of $R^{12}$ and $R^{13}$ in the formulas [VI] and [VII] represents —$OR^{01}$ and the other represents a hydrogen atom wherein $R^{01}$ represents acyl groups such as acetyl group, propionyl group, butanoyl group and benzoyl group or a hydrogen atom. $R^{14}$ in the formula [VIII] represents acyl groups such as acetyl group, propionyl group, butanoyl group, and benzoyl group or a hydrogen atom. One of $R^{15}$ and $R^{16}$ represents —$OR^{14}$ and the other represents a hydrogen atom wherein $R^{14}$ is as defined above.

The process for producing 2-α-glycoside compound of sialic acid according to the present invention is carried out substantially in the following manner.

First, an alkylthiosialic acid derivative represented by the formula [I] disclosed in Japanese Patent Kokai No. 63-41494 and the like as a sugar donor for formation of glycoside is reacted with a compound having an alcoholic hydroxyl group in a polar solvent (desirably fully dried) having no hydroxyl group such as, for example, acetonitrile, propionitrile, butyronitrile or nitromethane in the presence of an ester of trifluoromethane sulfonic acid such as, for example, methyl triflate (methyl trifluoromethanesulfonate), trimethylsilyl triflate (trimethylsilyl trifluoromethanesulfonate) or DMTST at a low temperature, for example, room temperature or lower, preferably −5° C. or lower for several hours to several tens of hours. The compound having an alcoholic hydroxyl group includes, for example, compounds represented by the above-mentioned formulas [II], [III], [IV] and [V], but this is not critical and any of those which have primary or secondary hydroxyl group can be used. After the termination of the reaction, the reaction mixture may be subjected to after-treatment in accordance with a conventional manner, for example, by removing insoluble matters by filtration and concentrating the filtrate. If necessary, purification may be carried out, for example, by column chromatography.

According to the process of the present invention 2-α-O-glycoside of sialic acid can be obtained in markedly high yields and substantially no production of 2-β-O-glycoside is recognized. Besides, according to the process of the present invention, hydroxyl group of acceptor may be either primary one or secondary one. Japanese Patent Kokai No. 63-41494 has reported that when the alkylthiosialic acid derivative is reacted with a primary alcohol in a non-polar solvent such as dichloromethane, only β-O-glycoside is obtained from both the α-SMe derivative and the β-SMe derivative. Therefore, it is surprising that when as in the present invention, an alkylthiosialic acid derivative as shown in the formula [I] is reacted with a compound having an alcoholic hydroxyl group in a polar solvent having no hydroxyl group such as acetonitrile at a low temperature, α-O-glycoside can be selectively obtained with either primary or secondary hydroxyl group.

The compound represented by the formula [II] can be easily obtained, for example, by reacting a compound represented by the formula [IIa]:

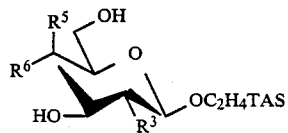

(wherein $R^3$, $R^5$, $R^6$ and TAS are as defined above) with an acylating agent (e.g., benzoyl chloride and acetic anhydride) in accordance with ordinary acylation method, for example, in the presence of a base such as pyridine or triethylamine, if necessary, under cooling or by reacting a compound represented by the formula [IIa] with di-n-butyltin oxide, tetra-n-butylammonium bromide and benzyl bromide in a non-polar solvent such as benzene, toluene, chloroform or dichloroethane for 1-10 hours under heating in accordance with ordinary method of benzylation of hydroxyl group. Compounds obtained by the former method are compounds in which $R^4$ in the formula [II] is an acyl group such as benzoyl group or acetyl group and compounds obtained by the latter method are compounds in which $R^4$ in the formula [II] is benzyl group. These compounds are all novel compounds not disclosed in any literature.

The compound represented by the formula [III] can be easily obtained, for example, in the following manner.

That is, first, a compound represented by the formula [II] where $R^4$ is benzyl group is prepared by the latter method mentioned above using a compound represented by the formula [IIa] as a starting material. Then, the resulting compound is reacted with an acylating agent (e.g., benzoyl chloride and acetic anhydride) in accordance with ordinary acylation method in the presence of a base such as pyridine or triethylamine, if necessary, under cooling to selectively acylate the hydroxyl group at 6-position to obtain a compound represented by the formula [IIIa]:

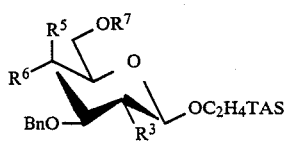

(wherein $R^3$, $R^5$, $R^6$, $R^7$, and TAS are as defined above and Bn represents a benzyl group). Then, this compound is reduced in accordance with conventional method using, for example, formic acid as a hydrogen donor and palladiumcarbon as a catalyst to obtain the compound of the present invention represented by the formula [III] with maintaining the modification group at 6-position and with only the benzyl group at 3-position being eliminated. This compound is also a novel compound never disclosed in literatures.

The compound represented by the formula [IV] can be easily prepared, for example, by the following method.

That is, first, a compound represented by the formula [IVa]:

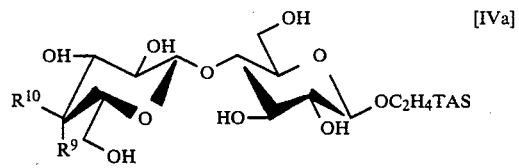

(wherein $R^9$, $R^{10}$ and TAS are as defined above) is reacted with di-n-butyltin oxide, tetra-n-butylammonium bromide and benzyl bromide in a non-polar solvent such as benzene, toluene, chloroform or dichloroethane for 1-10 hours under heating in accordance with ordinary method of benzylation of hydroxyl group to obtain a compound represented by the formula [IVb]:

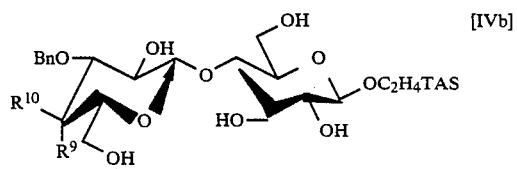

(wherein $R^9$, $R^{10}$, TAS and Bn are as defined above). Then, in accordance with ordinary acylation method, this compound is reacted with an acylating agent (e.g., benzoyl chloride and acetic anhydride) in the presence of a base such as pyridine or triethylamine, if necessary, under cooling to selectively acylate the hydroxyl groups at 2-position, 6-position and 6'-position to obtain a compound represented by the formula [IVc]:

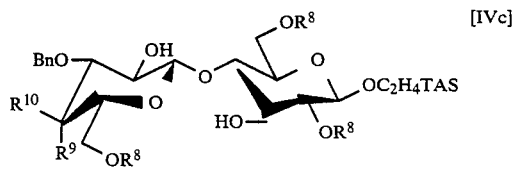

(wherein $R^8$, $R^9$, $R^{10}$, Bn and TAS are as defined above). Then, in accordance with conventional method, this compound is reduced using, for example, palladium-carbon as a catalyst and formic acid as a donor for hydrogen to obtain a compound represented by the formula [IV] with elimination of only the benzyl group at 3'-position.

The compounds represented by the formulas [IVb], [IVc] and [IV] are all novel compounds.

When the resulting compound represented by the formula [II], [III] or [IV] of the present invention is reacted with an alkylthiosialic acid derivative represented by the formula [I] which is a sugar donor in accordance with the process for production of 2-α-O-glycoside compounds of sialic acid according to the present invention, 2-α-O-glycoside compound of sialic acid represented by the formula [VI], [VII] or [VIII] of the present invention can be easily obtained.

That is, the compound of the present invention represented by the formula [VI] can be obtained in high yields by reacting the compound represented by the formula [II] with alkylthiosialic acid derivative represented by the formula [I] in accordance with the process of the present invention for the production of 2-α-O-glycoside compound of sialic acid. The compound of the present invention represented by the formula [VII] can be obtained in high yields by reacting the compound of the present invention represented by the formula [III] with alkylthiosialic acid derivative represented by the formula [I] in accordance with the process of the present invention for the production of 2-α-O-glycoside compound of sialic acid. Furthermore, the compound of the present invention represented by the formula [VIII] can be obtained in high yields by reacting the compound of the present invention represented by the formula [IV] with alkylthiosialic acid derivative represented by the formula [I] in accordance with the process of the present invention for the production of 2-α-O-glycoside compound of sialic acid. The compounds represented by the formulas [VI], [VII] and [VIII] are all novel compounds never disclosed in literatures.

The compound represented by the formula [IIa] which is a starting material for preparation of the compounds represented by the formulas [II] and [III] and the compound represented by the formula [IVa] which is a starting material for preparing the compound represented by the formula [IV] both can be easily obtained by the following method using the corresponding sugars or amino sugars which was found by the inventors (Japanese Patent Application No. 63-1707).

That is, first, the corresponding sugar or amino sugar is acylated by conventional method using an acylating agent (e.g., acetic anhydride and acetyl chloride) and then a halogen group is introduced at 1-position using hydrogen bromide or the like by conventional method, followed by reacting with TASC₂H₄OH (wherein TAS is as defined above) in the presence of a condensing agent such as Hg(CN)₂ and HgBr₂, Ag₂CO₃ and AgClO₄, Ag₂CO₃ and I₂, AgClO₄ or Hg(CN)₂ to obtain a sugar derivative or an amino sugar derivative where the hydroxyl group at 1-position is protected with 2-(trialkylsilyl)ethyl group and the other hydroxyl groups are protected with the acyl groups. The compound represented by the formula [IIa] or [IVa] can be easily obtained by subjecting the resulting sugar derivative or amino sugar derivative to deacylation by conventional method, for example, in methanol with sodium methylate.

The alkylthiosialic acid derivative represented by the formula [I] used in the process of the present invention can be easily prepared through the following route, for example, in accordance with the method disclosed in Japanese Patent Kokai No. 63-41494 and the thus obtained alkylthiosialic acid derivative may be used in the process.

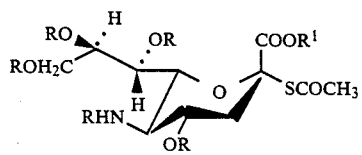

(wherein R and R¹ are as defined above).

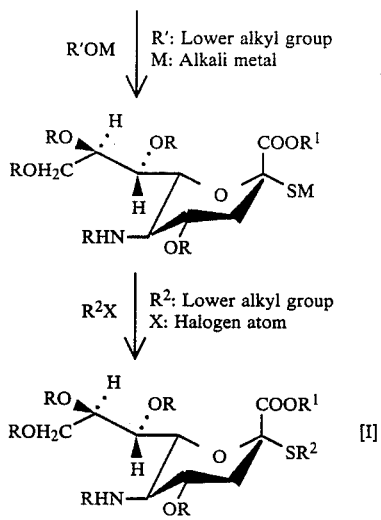

DMTST used in the process of the present invention is prepared as required from dimethyl disulfide and methyl trifluoromethanesulfonate in accordance with the method disclosed in J. Chem. Soc., Perkin Trans. II, 1569–1572 (1982).

The following nonlimiting examples illustrate the present invention.

The abbreviations used in the explanation of NMR have the following meanings.

Me: Methyl group; Ac: Acetyl group; Bz: benzoyl group

REFERENCE EXAMPLE 1

Preparation of 1-[2-(trimethylsilyl)-ethyl]-2,3,4,6-tetra-O-acetyl-β-D-galactopyranoside 5.04 g of 1,2,3,4,6-penta-O-acetyl-D-galactopyranoside was dissolved in 50 ml of sufficiently dehydrated dichloromethane and thereto was added 25 g of 30% acetic acid solution of hydrogen bromide at 0° C., followed by reaction with stirring at room temperature for 1.5 hours. After termination of the reaction, the reaction mixture was concentrated under reduced pressure to obtain a syrupy product. This was dissolved in 25 ml of dichloromethane and thereto was added 5 g of Molecular Sieves 4Å and reaction was allowed to proceed for 5 hours with stirring (Reaction mixture-1). Separately, 7 g of Ag₂CO₃, 2.7 g of AgClO₄, 3.66 ml of trimethylsilyl ethanol and 5 g of Molecular Sieves 4Å were suspended in 25 ml of sufficiently dehydrated dichloromethane and reaction was allowed to proceed for 5 hours with stirring (Reaction mixture-2). Then, reaction mixture-1 and reaction mixture-2 were mixed and reaction was allowed to proceed overnight with stirring. After the termination of the reaction, the reaction mixture was filtered through Celite and the filtrate was concentrated under reduced pressure to obtain a syrupy product. This was purified by column chromatography [packing material: Wakogel C-200 (trademark for packing material supplied by Wako Pure Chemical Industries LTD.), eluent: CH₂Cl₂] to obtain 4.2 g of syrup of 1-[2-(trimethylsilyl)ethyl]-2,3,4,6-tetra-O-acetyl-β-D-galactopyranoside. Yield: 72.5%.

Elementary analysis:

| Calcd. (%) C 50.88, H 7.19 |
|---|

-continued

Found (%) C 50.95, H 7.30
$[\alpha]_D = -9.49°$ (C = 1.01, CHCl$_3$)

REFERENCE EXAMPLE 2

Preparation of 1-[2-(trimethylsilyl)-ethyl]-β-D-galactopyranoside [hereinafter referred to as Compound (1)]

3.36 g of 1-[2-(trimethylsilyl)ethyl]-2,3,4,6-tetra-O-acetyl-β-D-galactopyranoside obtained in Reference Example 1 was dissolved in 30 ml of sufficiently dehydrated methanol and thereto was added a catalytic amount of sodium methylate, followed by stirring for 1 hour. After termination of the reaction, the reaction mixture was neutralized with Amberlite IR-120 (trademark for H$^+$ type ion exchange resin supplied by Organo Co.) and the product was subjected to filtration. The filtrate was concentrated under reduced pressure to quantitatively obtain a crystal of Compound (1).

Elementary analysis:
Calcd. (%) C 47.12, H 8.63
Found (%) C 47.35, H 8.71
$[\alpha]_D = -22.06°$ (C = 1.012, CH$_3$OH).

EXAMPLE 1

Preparation of 2-(trimethylsilyl)ethyl 3-O-benzoyl-β-D-galactopyranoside (compound of the formula [II] wherein R$^3$=—OH, R$^4$=benzoyl group, R$^5$=—OH, R$^6$=H, TAS=trimethylsilyl group, which is hereinafter referred to as Compound (2))

1.0 g of Compound (1) was dissolved in 10 ml of pyridine and the solution was cooled to −50° C. Thereto was added dropwise over 10 minutes a solution prepared by dissolving 603 mg of benzoyl chloride in 10 ml of dichloromethane and cooled to −50° C. Reaction was allowed to proceed for 3 hours with stirring and then to the reaction mixture was added methanol, followed by concentration. The residue was extracted with addition of dichloromethane. The dichloromethane layer was washed with water, dried over anhydrous Na$_2$SO$_4$ and then concentrated to obtain a syrup. This was purified by column chromatography [packing material: Wakogel C-200, eluent: CH$_2$Cl$_2$/CH$_3$OH=40/1] to obtain 920 mg of the objective Compound (2). Yield: 67%.

$[\alpha] = +30.50°$ (C = 1.20, CHCl$_3$)
IR $\nu_{max}^{film}$ (cm$^{-1}$): 3700 ~ 3100 (OH), 3000 ~ 2700 (CH), 1710 (ester), 860, 840 (trimethylsilylethyl), 710 (phenyl).
NMR (CDCl$_3$—CD$_3$OD) $\delta_{ppm}$: 8.08 ~ 7.38 (m, 5 H, —OBz), 5.04 (dd, 1H, J$_{2,3}$ = 10.26Hz, J$_{3,4}$ = 3.21Hz, H-3), 4.39 (d, 1H, H$_{1,2}$ = 7.70Hz, H-1), 4.25 (broad d, 1H, H-4), 4.01 (dd, 1H, H-2), 4.02 (m, 1H, —OCH$^2$CH$_2$Si), 3.61 (m, 1H, —OCH$^1$CH$_2$Si), 1.00 (m, 2H, —OCH$_2$CH$_2$Si), 0 (s, 9H, Me$_3$Si).

EXAMPLE 2

Preparation of 2-(trimethylsilyl)ethyl 3-O-benzyl-β-D-galactopyranoside (compound of the formula [II] wherein R$^3$=—OH, R$^4$=benzyl group, R$^5$=—OH, R$^6$=H and TAS=trimethylsilyl group, which is hereinafter referred to as Compound (3))

1.90 g of compound (1) was suspended in 50 ml of benzene and 2.54 g of (n—C$_4$H$_9$)$_2$SnO was added thereto, followed by stirring at 80° C. for 5 hours. Then, thereto were added 1.10 g of (n—C$_4$H$_9$)$_4$NBr and 12 ml of benzyl bromide and reaction was allowed to proceed for further 3 hours with stirring. After completion of the reaction, the reaction mixture was concentrated under reduced pressure. To the residue was added n-hexane and excess benzyl bromide was removed by decantation. The resulting syrup was subjected to column chromatography [packing material: Wakogel C-200, eluent: CH$_2$Cl$_2$/CH$_3$OH=125/1] to obtain 1.93 g of Compound (3). Yield: 76.6%.

$[\alpha]_D = +5.6$ (C = 0.50, CH$_2$Cl$_2$).
IR $\nu_{max}^{film}$ (cm$^{-1}$): 3700 ~ 3100 (OH), 3000 ~ 2700 (CH), 860, 840 (trimethylsilylethyl), 750, 700 (phenyl).
NMR (CDCl$_3$—CD$_3$OD) $\delta_{ppm}$: 7.26 ~ 7.38 (m, 5H, —CH$_2$C$_6$H$_5$), 4.67 ~ 4.77 (2d, 2H, —CH$_2$C$_6$H$_5$), 4.24 (d, 1H, J$_{1,2}$ = 7.7Hz, H-1), 4.02 (near m, 1H, J$_{3,4}$ = 3.3Hz, H-4), 3.80 (m, 2H, H-6), 3.70 (dd, 1H, H$_{2,3}$ = 9.53Hz, H-2), 3.60, 4.01 (2m, 2H, —OCH$_2$CH$_2$Si), 3.43 (near t, 1H, H-5), 3.39 (dd, 1H, H-3), 1.00 (m, 2H, —CH$_2$CH$_2$Si), 0 (s, 9H, Me$_3$Si).

EXAMPLE 3

Preparation of 2-(trimethylsilyl)ethyl 6-O-benzoyl-β-D-galactopyranoside (compound of the formula [III] wherein R$^3$=—OH, R$^5$=—OH, R$^6$=H, R$^7$=benzoyl group and TAS=trimethylsilyl group, which is referred to as Compound (5) hereinafter)

(1) Preparation of 2-(trimethylsilyl)ethyl 6-O-benzoyl-3-O-benzyl-β-D-galactopyranoside (hereinafter referred to as Compound (4))

3.5 g of Compound (3) obtained in the same manner as in Example 2 was dissolved in a mixed solvent of pyridine 10 ml and dichloromethane 40 ml, followed by cooling to −50° C. Thereto was added dropwise a solution prepared by dissolving 1.82 g of benzoyl chloride in 20 ml of dichloromethane and reaction was allowed to proceed for 1 hour with stirring. After termination of the reaction, to the reaction mixture was added methanol, followed by stirring for further 30 minutes and the reaction mixture was concentrated under reduced pressure. The residue was extracted with addition of dichloromethane and the dichloromethane layer was washed with water, dried over anhydrous Na$_2$SO$_4$ and then concentrated under reduced pressure. The resulting syrup was subjected to column chromatography [packing material: Wakogel C-200, eluent: CH$_2$Cl$_2$/CH$_3$OH=150/1] to obtain 3.16 g of Compound (4). Yield: 70.5%.

$[\alpha]_D = -1.55°$ (C = 0.900, CHCl$_3$).
IR $\nu_{max}^{film}$ (cm$^{-1}$: 3700 ~ 3150 (OH), 3150 ~ 2700 (CH), 1720, 1250 (ester), 860, 840 (trimethylsilyl), 710 (phenyl).
NMR (CDCl$_3$—CD$_3$OD) $\delta_{ppm}$: 8.08 ~ 7.29 (m, 10H, —CH$_2$C$_6$H$_5$, OBz), 4.77 (s, 2H, —CH$_2$—C$_6$H$_5$), 4.59 (near d, 2H, H-6,6'), 4.29 (d, 1H, J$_{1,2}$ = 7.88Hz, H-1), 4.00 (m, 2H, H-4, —OCH$^1$CH$_2$Si), 3.78 (m, 2H, H-2, H-5), 3.62 (m, 2H, —OCH$^2$CH$_2$Si), 3.47 (dd, 1H, J$_{2,3}$ = 9.43Hz, J$_{3,4}$ = 3.30Hz, H-3), 1.03 (m, 2H, —OCH$_2$CH$_2$Si), 0 (s, 9H, Me$_3$Si).

(2) Preparation of Compound (5)
3.50 g of Compound (4) was dissolved in 150 ml of methanol and 6 g of 10% palladium-carbon and 2.5 ml of formic acid were added to the solution and reaction was allowed to proceed for 1 hour at 60° C. with stirring. After the reaction, the reaction mixture was filtered to remove insoluble matters and filtrate was concentrated under reduced pressure. The resulting syrup was purified by column chromatography [packing material: Wakogel C-200, eluent: $CH_2Cl_2/CH_3OH=40/1$] to obtain 1.90 g of Compound (5). Yield: 67%.

---

$[\alpha]_D = -3.69°$ (C = 0.92, $CHCl_3$).
IR $\nu_{max}^{film}$ ($cm^{-1}$): 3700 ~ 3000 (OH), 3000 ~ 2800 (CH), 1720, 1250 (ester), 860, 840 (trimethylsilyl), 700 (phenyl).
NMR ($CDCl_3$—$CD_3OD$) $\delta_{ppm}$: 8.07 ~ 7.43 (m, 5H, OBz) 4.59 (d, 2H, J = 6.39Hz, H-6, H-6'), 4.29 (d, 1H, $J_{1,2}$ = 7.33Hz, H-1), 3.84 (near t, 1H, $J_{5,6}$ = 6.60Hz, H-5), 1.03 (m, 2H, $-OCH_2CH_2Si$), 0 (s, 9H, $Me_3Si$).

---

EXAMPLE 4

Preparation of 2-(trimethylsilyl)ethyl O-(6-O-benzoyl-β-D-galactopyranosyl)-(1→4)-2,6-di-O-benzoyl-β-D-glucopyranoside (compound of the formula [IV] wherein $R^8$=benzoyl group, $R^9$=—OH, $R^{10}$=H and TAS=trimethylsilyl group, which is referred to as Compound (8) hereinafter)

(1) Preparation of 2-(trimethylsilyl)ethyl O-(3-O-benzyl-β-D-galactopyranosyl)-(1→4)-β-D-glucopyranoside (hereinafter referred to as Compound (6))

6.59 g of 2-(trimethylsilyl)ethyl β-D-lactoside was dissolved in 100 ml of methanol. To the solution was added 4.92 g of $(n-C_4H_9)_2SnO$ and reaction was allowed to proceed for 3 hours with stirring under reflux with heating. After the reaction, the reaction mixture was concentrated under reduced pressure and sufficiently dried. Then, 200 ml of benzene was added to the residue to dissolve it. Thereto were added 4.80 g of $(n-C_4H_9)_4NBr$ and 14.2 ml of benzyl bromide and reaction was allowed to proceed for 3 hours with stirring under reflux with heating. After termination of the reaction, the reaction mixture was concentrated under reduced pressure. n-Hexane was added to the residue and excess benzyl bromide was removed by decantation. The resulting syrup was subjected to column chromatography [packing material: Wakogel C-200, eluent: ethyl acetate/n-hexane=4/1] to obtain 5.96 g of Compound (6). Yield: 75.2%.

--- m.p. 164–167° C.
$[\alpha]_D = -0.14°$ (C = 1.48, $CH_2Cl_2$)
IR $\nu_{max}^{film}$ ($cm^{-1}$): 3700 ~ 3100 (OH), 3000 ~2850 (CH), 860, 840 (trimethylsilyl) 740, 700 (phenyl).
NMR ($CD_3OD$) $\delta_{ppm}$: 7.41 ~ 7.21 (m, 5H, $-CH_2-C_6H_5$), 4.72, 4.58 (2d, 2H, $J_{gem}$ = 11.9Hz, $-CH_2-C_6H_5$), 4.34 (d, 1H, $H_{1',2'}$ = 8.1Hz, H-1'), 4.26 (d, 1H, $J_{1,2}$ = 7.7Hz, H-1), 3.97 (near d, 1H, $J_{3',4'}$ = 3.3Hz, H-4'), 3.35 (dd, 1H, $J_{2',3'}$ = 9.5Hz, H-3'), 3.21 (near t, 1H, $J_{2,3}$ = 8Hz, H-2), 0.96 (m, 2H, $-OCH_2CH_2Si$), -0.02 (s, 9H, $SiMe_3$).

---

1.32 g of Compound (6) was dissolved in a mixed solvent of pyridine 8 ml and dichloromethane 20 ml, followed by cooling to −50° C. Thereto was added dropwise a solution prepared by dissolving 1.2 ml of benzoyl chloride in 15 ml of dichloromethane and reaction was allowed to proceed for 30 minutes with stirring. After termination of the reaction, to the reaction mixture was added methanol to decompose excess benzoyl chloride. Thereafter, the reaction mixture was concentrated under reduced pressure. The residue was extracted with addition of dichloromethane and the dichloromethane layer was washed with hydrochloric acid and water, dried over anhydrous $Na_2SO_4$ and then concentrated under reduced pressure. The resulting syrup was subjected to column chromatography [packing material: Wakogel C-200, eluent: $CH_2Cl_2/CH_3OH=200/1$] to obtain 1.40 g of Compound (7). Yield: 67%.

---

$[\alpha]_D = +14.01$ (C = 0.856, $CHCl_3$).
IR $\nu_{max}^{film}$ ($cm^{-1}$): 3700~3100 (OH), 3100~2800 (CH), 1730, 1260 (ester), 860, 840 (trimethylsilyl), 710 (phenyl).
NMR ($CDCl_3$—$CD_3OD$) $\delta_{ppm}$: 8.18~7.38 (m, 20H, OBz × 3, $-CH_2-C_6H_5$), 5.33 (dd, 1H, $H_{1,2}$ = 8.06Hz, $H_{2,3}$ = 8.15Hz, H-2), 5.04 (dd, 1H, $J_{gem}$ = 11.91Hz, H-6), 4.85 (s, 2H, $-CH_2-C_6H_5$), 4.73 (d, 1H, $J_{1,2}$ = 8.06Hz, H-1), 4.63 (dd, 1H, $J_{gem}$ = 11.90Hz, $J_{5,6}$ = 5.86Hz, H-6), 4.51 (d, 1H, $J_{1',2'}$ = 7.88Hz, H-1'), 3.53 (dd, 1H, $J_{2',3'}$ = 9.53, $J_{3',4'}$ 3.30Hz, H-3'), 0.96 (m, 2H, $-OCH_2CH_2Si$), 0 (s, 9H, $Me_3Si$)

---

(3) Preparation of Compound (8)

1.40 g of Compound (7) was dissolved in 50 ml of methanol and 1.0 g of 10% palladium-carbon and 1 ml of formic acid were added to the solution and reaction was allowed to proceed for 2 hours at 60° C. with stirring. After the reaction, the reaction mixture was filtered to remove insoluble matters and filtrate was concentrated under reduced pressure. The resulting syrup was subjected to column chromatography [packing material: Wakogel C-200, eluent: $CH_2Cl_2/CH_3OH=50/1$] to obtain 880 mg of Compound (8). Yield: 70%.

---

$[\alpha]_D = +11.03°$ (C = 0.58, $CHCl_3$).
IR $\nu_{max}^{film}$ ($cm^{-1}$): 3700~3100 (OH), 3000~2800 (CH), 1720, 1260 (ester), 860, 840 (trimethylsilyl), 700 (phenyl).
NMR ($CDCl_3$—$CD_3OD$) $\delta_{ppm}$: 8.17–7.40 (m, 15H, OBz × 3), 5.33 (dd, 1H, $J_{1,2}$ = 8.06Hz, $J_{2,3}$ = 9.61Hz, H-2), 4.99 (dd, 1H, $J_{gem}$ = 10.26Hz, H-6), 4.81(dd, 1H, $J_{gem}$ = 11.91Hz, $J_{5,6}$ = 3.30Hz, H-6), 4.74 (d, 1H, $J_{1',2'}$ = 8.06Hz, H-1), 4.64 (dd, 1H, $J_{gem}$ = 11.90Hz, $J_{5,6}$ = 5.86Hz, H-6), 4.50 (d, 1H, $J_{1',2'}$ = 7.88Hz, H-1').

---

EXAMPLE 5

Preparation of 2-(trimethylsilyl)ethyl O-[methyl (5-acetamido-4,7,8,9-tetra-O-acetyl-3,5-dideoxy-D-glycero-α-D-galacto-2-nonulopyranosyl)onate]-(2→6)-3-O-benzoyl-β-D-galactopyranoside (compound of the formula [VI] wherein R=acetyl group, $R^1$=methyl group, $R^3$=OH, $R^4$=benzoyl group, $R^{12}$=—OH, $R^{13}$=H and TAS=trimethylsilyl group, which is hereinafter referred to as Compound (9))

0.16 g of Compound (2) obtained in Example 1 and 0.43 g of methyl (methyl 5-acetamido-4,7,8,9-tetra-O-acetyl-3,5-dideoxy-2-thio-D-glycero-α-D-galacto-2-nonulopyranoside)onate (compound of the formula [I] wherein R=acetyl group, $R^1$=methyl group and $R^2$=methyl group, which is hereinafter referred to as Compound (10)) were dissolved in 2.5 ml of anhydrous acetonitrile and then thereto was added 0.40 g of Molecular Sieves 3 Å, followed by stirring for 5 hours. Thereto was added 3.4 g of Molecular Sieves 3 Å containing 1.7 g of DMTST at −10° C. ~ −15° C. and reaction was allowed to proceed for 24 hours at that temperature with stirring. After completion of the reaction, the reaction mixture was filtered through Celite and the filtrate was extracted with addition of dichloromethane. The dichloromethane layer was washed with aqueous sodium carbonate solution and water, dried over anhydrous $Na_2SO_4$ and then concentrated under reduced pressure. The resulting syrup was subjected to column chromatography [packing material: Wakogel C-200, eluents: toluene/$CH_3OH$=20/1 and ethyl acetate/n-hexane=1/1] to obtain 0.243 g of Compound (9). Yield: 68%.

$[\alpha]_D = -6.36°$ (C = 2.42, $CH_2Cl_2$).
IR $\nu_{max}^{film}$ (cm$^{-1}$): 3700 ~ 3100 (OH, NH), 3100 ~ 2800 (CH), 1750, 1220 (ester), 1660, 1550 (amide), 860, 840 (trimethylsilyl), 710 (phenyl).
NMR ($CDCl_3$—$CD_3OD$) $\delta_{ppm}$: galactose unit;
8.10 ~ 7.39 (m, 5H, OBz), 4.99 (dd, 1H, $H_{2,3}$ = 10.07Hz, $J_{3,4}$ = 3.30Hz, H-3), 4.38 (d, 1H, $J_{1,2}$ = 7.88Hz, H-1), 4.15 (d, 1H, H-4), 1.04 (m, 2H, —$OCH_2CH_2Si$), 0 (s, 9H, $Me_3Si$).
Sialic acid unit: 5.33 ~ 5.24 (m, 2H, H-7, H-8), 4.76 (ddd, 1H, $H_{3e,4}$ = 4.68Hz, H-4), 4.36 (dd, 1H, $J_{8,9}$ = 2.57Hz, $J_{9,9'}$ = 12.09Hz, H-9), 2.56 (dd, 1H, $J_{3e,3a}$ = 12.73Hz, H-3e), 2.10, 2.08, 1.98, 1.93, 1.82 (5s, 15H, OAc × 4, NHAc).

$\beta$-Glycoside of sialic acid was not obtained at all in this Example.

EXAMPLE 6

Preparation of 2-(trimethylsilyl)ethyl O-[methyl(5-acetamido-4,7,8,9-tetra-O-acetyl-3,5-dideoxy-D-glycero-$\alpha$-D-galacto-2-nonulopyranosyl)onate]-(2→6)-2,4-di-O-acetyl-3-O-benzoyl-$\beta$-D-galactopyranoside (compound of the formula [VI] wherein R=acetyl group, $R^1$=methyl group, $R^3$=—$OCOCH_3$, $R^4$=benzoyl group, $R^{12}$=—$OCOCH_3$, $R^{13}$=H, and TAS=-trimethylsilyl group, which is hereinafter referred to as Compound (11))

0.200 g of Compound (9) obtained in Example 5 was dissolved in 6 ml of anhydrous pyridine and 4 ml of acetic anhydride was added thereto and the mixture was left to stand overnight to allow reaction to proceed. After termination of the reaction, methanol was added to the reaction mixture to decompose excess acetic anhydride, followed by concentration under reduced pressure. The resulting syrup was subjected to column chromatography [packing material: Wakogel C-200, eluent: $CH_2Cl_2$/$CH_3OH$=80/1] to quantitatively obtain Compound (11).

$[\alpha]_D = -7.17°$ (C = 1.70, $CHCl_3$)
IR $\nu_{max}^{film}$ (cm$^{-1}$): 3700~3100 (NH), 3100~2800 (CH), 1750, 1220 (ester), 860, 840 (trimethylsilyl), 710 (phenyl).
NMR ($CDCl_3$) $\delta_{ppm}$: galactose unit: 7.92~7.36 (m, 5H, OBz), 5.62 (broad d, 1H, $J_{3,4}$ = 2.39Hz, H-4), 5.35 (dd, 1H, $J_{1,2}$ = 7.87Hz, $J_{2,3}$ = 10.44Hz, H-2), 5.22 (dd, 1H, $J_{3,4}$ = 3.48Hz, H-3), 4.62 (d, 1H, $J_{1,2}$ = 7.88Hz, H-1), 3.81 (dd, 1H, $J_{5,6}$ = 5.87Hz, $J_{6,6'}$ = 10.26Hz, H-6), 3.41 (dd, 1H, $J_{5,6'}$ 7.79Hz, H-6'). Sialic acid unit: 5.39~5.20 (m, 3H, H-7, H-8, NH), 4.83 (ddd, 1H, $J_{3e,4}$ = 4.58Hz, H-4), 4.33 (dd, 1H, $J_{8,9}$ = 2.66Hz, $J_{9,9'}$ = 12.64Hz, H-9), 3.75 (s, 3H, —COOME), 2.50 (dd, 1H, $J_{3e,3a}$ = 12.82Hz, H-3e), 2.17, 2.10, 2.06, 2.01, 1.99, 1.96, 1.86 (7s, 21H, OAc × 6, NHAc), 0.94 (m, 2H, —$CH_2CH_2Si$), 0 (s, 9H, $Me_3Si$).

EXAMPLE 7

Preparation of 2-(trimethylsilyl)ethyl O-[methyl (5-acetamido-4,7,8,9-tetra-O-acetyl-3,5-dideoxy-D-glycero-$\alpha$-D-galacto-2-nonulopyranosyl)onate]-(2→3)-6-O-benzoyl-$\beta$-D-galactopyranoside (compound of the formula [VII] where R=acetyl group, $R^1$=methyl group, $R^3$=—OH, $R^7$=benzoyl group, $R^{12}$=—OH, $R^{13}$=H, TAS=trimethylsilyl group, which is hereinafter referred to as Compound (12)).

0.43 g of Compound (10) and 0.16 g of Compound (5) obtained in Example 3 were dissolved in 2.5 ml of anhydrous acetonitrile and thereto was added 0.40 g of Molecular Sieves 3 Å, followed by stirring for 5 hours. Thereto was added 3.4 g of Molecular Sieves 3 Å containing 1.7 g of DMTST at $-10°$ C.~$-15°$ C. and reaction was allowed to proceed for 24 hours at the same temperature with stirring. After termination of the reaction, the reaction mixture was filtered through Celite and the filtrate was extracted with addition of dichloromethane. The dichloromethane layer was washed with aqueous sodium carbonate solution and water, dried over anhydrous $Na_2SO_4$ and concentrated under reduced pressure. The resulting syrup was subjected to column chromatography [packing material: Wakogel C-200, eluents: ethyl acetate/n-hexane=1/1 and $CH_2Cl_2$/$CH_3OH$=60/1] to obtain 0.143 g of Compound (12). Yield: 40%.

$[\alpha]_D = -5.98°$ (C = 2.04, $CHCl_3$).
IR $\nu_{max}^{film}$ (cm$^{-1}$): 3700~3150 (OH, NH), 3150~2700 (CH), 1750, 1230 (ester), 1670, 1550 (amide), 860, 840 (trimethylsilyl), 720 (phenyl).
NMR ($CDCl_3$—$CD_3OD$) $\delta_{ppm}$: galactose unit:
8.07~7.29 (m, 5H, OBz), 1.00 (m, 2H, —$OCH_2CH_2Si$), 0 (s, 9H, $Me_3Si$). Sialic acid unit: 4.88 (m, 1H, H-4), 3.77 (s, 3H, COOMe), 2.60 (m, 1H, H-3e).

$\beta$-Glycoside of sialic acid was not obtained at all in this Example, too.

EXAMPLE 8

Preparation of 2-(trimethylsilyl)ethyl O-[methyl (5-acetamido-4,7,8,9-tetra-O-acetyl-3,5-dideoxy-D-glycero-$\alpha$-D-galacto-2-nonulopyranosyl)onate]-(2→3)-2,4-di-O-acetyl-6-O-benzoyl-$\beta$-D-galactopyranoside (compound of the formula [VII] where R=acetyl group, $R^1$=methyl group, $R^3$=—$OCOCH_3$, $R^7$=benzoyl group, $R^{12}$=—$OCOCH_3$, $R^{13}$=H and TAS=-trimethylsilyl group, which is hereinafter referred to as Compound (13)).

Compound (12) obtained in Example 7 was acetylated in the same manner as acetylation of Compound (9) in Example 6 and treated by column chromatography in the same manner as in Example 6 to quantitatively obtained Compound (13).

$[\alpha]_D = -24.51°$ C = 2.66, $CHCl_3$).
IR $\nu_{max}^{film}$ (cm$^{-1}$): 3700~3100 (NH), 3100~2700 (CH) 1750, 1230 (ester), 1660, 1540 (amide), 860, 840 (trimethylsilyl), 720 (phenyl).
NMR ($CDCl_3$—$CD_3CD$) $\delta_{ppm}$: galactose unit:
8.04~7.43 (m, 5H, OBz), 0.98 (m, 2H, —$OCH_2CH_2Si$), 0 (s, 9H, $Me_3Si$). Sialic acid unit: 4.85 (m, 1H, H-4), 3.77 (s, 3H, —COOMe), 2.59 (m, 1H, H-3e), 2.22~1.83 (m, 21H, OAc × 6, NHAc).

EXAMPLE 9

Preparation of 2-(trimethylsilyl)ethyl O-[methyl (5-acetamido-4,7,8,9-tetra-O-acetyl-3,5-dideoxy-D-glycero-$\alpha$-D-galacto-2-nonulopyranosyl)onate]-(2→3)-

O-(6-O-benzoyl-β-D-galactopyranosyl)-(1→4)-2,6-di-O-benzoyl-β-D-glucopyranoside (compound of the formula [VIII] where R=acetyl group, R¹=methyl group, R⁸=benzoyl group, R¹⁴=H, R¹⁵=OH, R¹⁶=H and TAS=trimethylsilyl group, which is hereinafter referred to as Compound (14)).

0.21 g of Compound (10) and 0.15 g of Compound (8) obtained in Example 4 were dissolved in 2.0 ml of anhydrous acetonitrile and thereto was added 0.30 g of Molecular Sieves 3 Å, followed by stirring overnight. Thereto was added 1.14 g of Molecular Sieves 3 Å containing 0.68 g of DMTST at −10° C.~−15° C. and reaction was allowed to proceed for 24 hours at the same temperature with stirring. After termination of the reaction, the reaction mixture was filtered through Celite and the filtrate was extracted with addition of dichloromethane. The dichloromethane layer was washed with aqueous sodium carbonate solution and water, dried over anhydrous Na₂SO₄ and concentrated under reduced pressure. The resulting syrup was subjected to column chromatography [packing material: Wakogel C-200, eluent: ethyl acetate/n-hexane=4/1] to obtain 0.097 g of Compound (14). Yield: 40%.

---

$[\alpha]_D = +10.9°$ (C = 1.74, CHCl₃).
IR $\nu_{max}^{film}$ (cm⁻¹): 3700~3100 (OH, NH), 3100~2700 (CH) 1730, 1220 (ester), 1650, 1540 (amide), 850, 830 (trimethylsilyl), 710 (phenyl).
NMR (CDCl₃—CD₃OD) $\delta_{ppm}$: lactose unit: 8.20~7.46 (m, 15H, OBz × 3), 5.36 (dd, 1H, $J_{1,2}$ = 8.24Hz, $J_{2,3}$ = 9.52Hz, H-2), 5.09 (dd, 1H, $J_{gem}$ = 10.26Hz, H-6), 4.83 (dd, 1H, $J_{gem}$ = 11.91, $J_{5,6}$ = 3.30Hz, H-6), 4.77 (d, 1H, $J_{1,2}$ = 8.06Hz, H-1), 4.72 (d, 1H, $J_{1,2}$ = 7.69Hz, H-1'), 4.62 (dd, 1H, $J_{gem}$ = 11.91Hz, $J_{5,6}$ = 5.86Hz, H-6), 3.69 (ddd, 1H, —CHCH₂Si), 0.98 (m, 2H, —CH₂CH₂Si), 0 (s, 9H, Me₃Si). Sialic acid unit: 5.42 (m, 2H, H-7, H-8), 4.97 (ddd, 1H, H-4), 3.92 (s, 3H, —COOMe), 2.81 (dd, 1H, $J_{3e,4}$ = 4.49Hz, $J_{3e,3a}$ = 12.73Hz, H-3e), 2.31~1.99 (5s, 15H, OAc × 4, NHAc).

---

β-Glycoside of sialic acid was not obtained at all in this Example, too.

EXAMPLE 10

Preparation of 2-(trimethylsilyl)ethyl O-[methyl (5-acetamido-4,7,8,9-tetra-O-acetyl-3,5-dideoxy-D-glycero-α-D-galacto-2-nonulopyransyl)onate]-(2→3)-O-(2,4-di-O-acetyl-6-O-benzoyl-β-D-galactopyranosyl)-(1→4)-3-O-acetyl-2,6-di-O-benzoyl-β-D-glucopyranoside (compound of the formula [VIII] where R=acetyl group, R¹=methyl group, R⁸=benzoyl group, R¹⁴=acetyl group, R¹⁵=—OCOCH₃, R¹⁶=H and TAS=trimethylsilyl group, which is hereinafter referred to as Compound (15)).

85 mg of Compound (14) obtained in Example 9 was dissolved in 8 ml of anhydrous pyridine and thereto was added 4 ml of acetic anhydride. This was left to stand overnight to allow reaction to proceed. After termination of the reaction, methanol was added to decompose excess acetic anhydride and the reaction mixture was concentrated under reduced pressure. The resulting syrup was subjected to column chromatography [packing material: Wakogel C-200, eluent: CH₂Cl₂/CH₃OH=60/1] to obtain 87 mg of Compound (15). Yield: 94%.

---

$[\alpha]_D = +5.74°$ (C = 1.74, CHCl₃).
IR $\nu_{max}^{film}$ (cm⁻¹): 3700~3200 (NH), 3100~2800 (CH) 1750, 1230 (ester), 1660, 1540 (amide), 860, 840 (trimethylsilyl), 720 (phenyl).
NMR (CDCl₃—CD₃OD) $\delta_{ppm}$: lactose unit: 8.18~7.50 (m, 15H, Bz × 3), 5.59 (t, 1H, $J_{2,3}$ = $J_{3,4}$ = 9.71Hz, H-3), 5.32 (dd, 1H, $J_{1,2}$ = 7.88Hz, H-2), 5.13 (dd, 1H, $J_{1,2'}$ = 7.87Hz, $J_{2',3'}$ = 10.17Hz, H-2), 5.13 (d, 1H, $J_{3,4}$ = 3.30, 1H, H-4'), 5.00 (d, 1H, $J_{1,2}$ = 7.88Hz, H-1), 4.81 (d, 1H, $J_{1,2}$ = 7.88Hz, H-1), 4.74 (dd, 1H, $J_{2',3'}$ = 10.17Hz, $J_{3',4'}$ = 3.30Hz, H-3'), 0.98 (m, 2H, —CH₂CH₂Si), 0 (s, 9H, Me₃Si). Sialic acid unit: 5.64 (m, 1H, H-8), 5.45 (dd, 1H, $J_{7,8}$ = 8.80Hz, $J_{6,7}$ = 2.57Hz, H-7), 4.94 (ddd, 1H, $J_{3e,4}$ = 4.76Hz, H-4), 3.83 (s, 3H, —COOMe), 2.68 (dd, 1H, $J_{3e,3a}$ = 12.64Hz, H-3e), 2.35~1.94 (8s, 24H, OAc × 7, NHAc).

---

The present invention has a conspicuous effect in that there has been provided, for the first time, a process for obtaining selectively and in high yields a 2-α-O-glycoside compound of sialic acid which is useful as starting material or intermediate for various medicines and biochemical agents such as ganglioside and its analogues.

What is claimed is:

1. A process for producing a 2-α-O-glycoside compound of sialic acid which comprises reacting an alkylthiosialic acid derivative represented by the formula [I]:

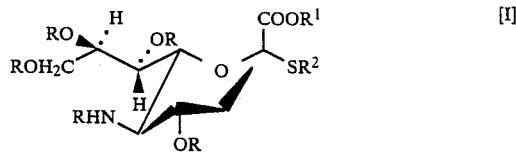

wherein R represents an acyl group and R¹ and R² each represents a lower alkyl group, with a compound having alcoholic hydroxyl group at a low temperature in a polar solvent having no hydroxyl group in the presence of a thiophilic promoter.

2. A process according to claim 1 wherein the thiophilic promoter is selected from the group consisting of methyl triflate, dimethyl(methylthio)sulfonium triflate and trimethylsilyl triflate.

3. A process according to claim 1, wherein the compound having alcoholic hydroxyl group is a compound represented by the formula [II]:

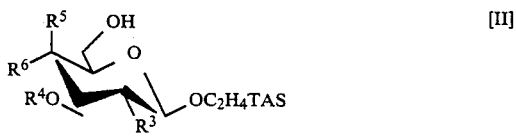

wherein R³ represents —OH, —NH₂; —OR⁰ or —NHR⁰ where R⁰ represents an acyl group, R⁴ represents a protecting group for hydroxyl group, one of R⁵ and R⁶ represents a hydroxyl group and the other represents a hydrogen atom and TAS represents a trialkylsilyl group.

4. A process according to claim 1, wherein the compound having alcoholic hydroxyl group is a compound represented by the formula [III]:

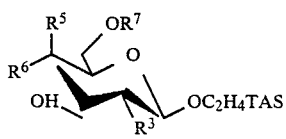
[III]

wherein $R^7$ represents an acyl group and $R^3$, $R^5$, $R^6$ and TAS are as defined above.

5. A process according to claim 1, wherein the compound having alcoholic hydroxyl group is a compound represented by the formula [IV]:

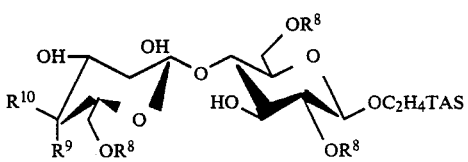
[IV]

wherein $R^8$ represents an acyl group, one of $R^9$ and $R^{10}$ represents a hydroxyl group and the other represents a hydrogen atom and TAS is as defined above.

6. A process according to claim 1, wherein the compound having alcoholic hydroxy group is an aliphatic alcohol represented by the formula [V]:

$$R^{11}OH \qquad [V]$$

wherein $R^{11}$ represents an alkyl group.

7. A compound represented by the formula [II]:

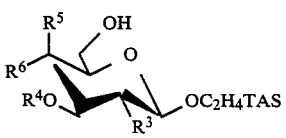
[II]

wherein $R^3$, $R^4$, $R^5$, $R^6$ and TAS are as defined above.

8. A compound represented by the formula [III]:

[III]

wherein $R^3$, $R^5$, $R^6$, $R^7$ and TAS are as defined above.

9. A compound represented by the formula [IV]:

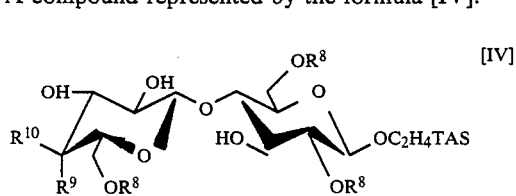
[IV]

wherein $R^8$, $R^9$, $R^{10}$ and TAS are as defined above.

10. A compound represented by the formula [VI]:

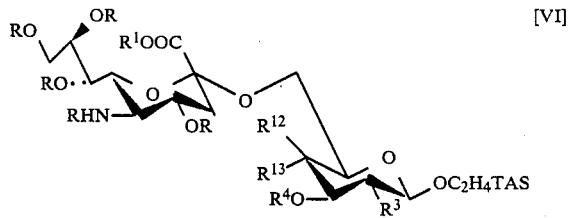
[VI]

wherein one of $R^{12}$ and $R^{13}$ represents $-OR^{01}$ and the other represents a hydrogen atom where $R^{01}$ represents an acyl group or a hydrogen atom, and R, $R^1$, $R^3$, $R^4$ and TAS are as defined above.

11. A compound represented by the formula [VII]:

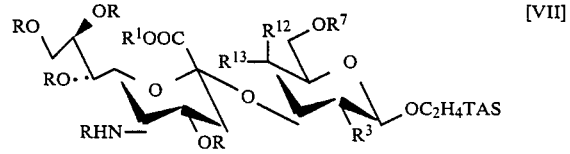
[VII]

wherein R, $R^1$, $R^3$, $R^7$, $R^{12}$, $R^{13}$ and TAS are as defined above.

12. A compound represented by the formula [VIII]:

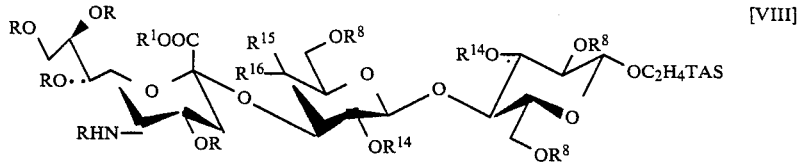
[VIII]

wherein $R^{14}$ represents an acyl group or a hydrogen atom, one of $R^{15}$ and $R^{16}$ represents $-OR^{14}$ and the other represents a hydrogen atom wherein $R^{14}$ is as defined above and R, $R^1$, $R^8$ and TAS are as defined above.

* * * * *

UNITED STATES PATENT AND TRADEMARK OFFICE
CERTIFICATE OF CORRECTION

PATENT NO. : 4,914,035
DATED : April 3, 1990
INVENTOR(S) : HASEGAWA et al

It is certified that error appears in the above-identified patent and that said Letters Patent is hereby corrected as shown below:

Column 2, lines 23 - 31, formula [I] should read:

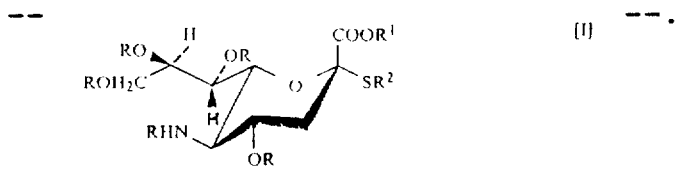

Signed and Sealed this

Twenty-ninth Day of October, 1991

Attest:

HARRY F. MANBECK, JR.

*Attesting Officer*    *Commissioner of Patents and Trademarks*